United States Patent
Abe

(10) Patent No.: US 10,463,280 B2
(45) Date of Patent: Nov. 5, 2019

(54) EXAMINATION SYSTEM, MOBILE APPARATUS AND EXAMINATION METHOD

(71) Applicant: CANON KABUSHIKI KAISHA, Tokyo (JP)

(72) Inventor: Naoto Abe, Machida (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 235 days.

(21) Appl. No.: 15/381,312

(22) Filed: Dec. 16, 2016

(65) Prior Publication Data

US 2017/0181668 A1 Jun. 29, 2017

(30) Foreign Application Priority Data

Dec. 25, 2015 (JP) .................. 2015-253188

(51) Int. Cl.
| | |
|---|---|
| *A61B 5/1172* | (2016.01) |
| *A61B 5/00* | (2006.01) |
| *A61B 6/10* | (2006.01) |
| *G16H 30/20* | (2018.01) |
| *G16H 40/60* | (2018.01) |
| *A61B 6/00* | (2006.01) |
| *G01R 33/54* | (2006.01) |
| *G16H 50/20* | (2018.01) |

(52) U.S. Cl.
CPC .......... *A61B 5/1172* (2013.01); *A61B 5/0015* (2013.01); *A61B 5/0033* (2013.01); *A61B 5/742* (2013.01); *A61B 5/7405* (2013.01); *A61B 6/10* (2013.01); *G16H 30/20* (2018.01); *G16H 40/60* (2018.01); *A61B 5/002* (2013.01); *A61B 5/0095* (2013.01); *A61B 5/6898* (2013.01); *A61B 5/704* (2013.01); *A61B 6/54* (2013.01); *G01R 33/543* (2013.01); *G16H 50/20* (2018.01)

(58) Field of Classification Search
CPC ..... A61B 5/117; A61B 5/1172; A61B 5/1173; A61B 5/1174; A61B 5/176
See application file for complete search history.

(56) References Cited

U.S. PATENT DOCUMENTS

| | | | | |
|---|---|---|---|---|
| 4,394,773 | A | * | 7/1983 | Ruell .................. A61B 5/1172 310/318 |
| 2005/0076182 | A1 | * | 4/2005 | Minne .................... G06F 21/32 711/163 |

(Continued)

FOREIGN PATENT DOCUMENTS

| | | |
|---|---|---|
| JP | 2002-222256 | 8/2002 |
| JP | 2002-336268 | 11/2002 |

*Primary Examiner* — Paula J Stice
(74) *Attorney, Agent, or Firm* — Venable LLP

(57) ABSTRACT

Provided is an examination system including a mobile apparatus and an examination apparatus. The mobile apparatus includes: a biological object information storing unit configured to store biological object information; a reading unit configured to read biological object information; a comparing unit configured to compare the biological object information; and an outputting unit configured to output a result of comparison, and the examination apparatus includes: an examination information acquiring unit configured to acquire examination information; and a controlling unit configured to control the operation of the examination apparatus.

17 Claims, 7 Drawing Sheets

(56) References Cited

U.S. PATENT DOCUMENTS

| | | | |
|---|---|---|---|
| 2006/0066438 A1* | 3/2006 | Altounian | G06F 21/86 340/5.53 |
| 2007/0258626 A1* | 11/2007 | Reiner | A61B 5/1171 382/115 |
| 2014/0100437 A1* | 4/2014 | Luo | A61B 5/0095 600/407 |

* cited by examiner

EXAMINATION SYSTEM, MOBILE APPARATUS AND EXAMINATION METHOD

BACKGROUND OF THE INVENTION

Field of the Invention

The present invention relates to an examination system, a mobile apparatus and an examination method.

Description of the Related Art

In recent years medical examination apparatuses have advanced, and a plurality of new examination apparatuses have been implemented. Including apparatuses that are still in the R&D stage, a photoacoustic imaging apparatus, an ultrasonic imaging apparatus, an X-ray imaging apparatus, a CT apparatus, an MRI apparatus, a retinal camera and the like are available. In the case of performing examination using such an examination apparatus, the physician instructs the examinee on the examination content and the examination apparatus, and the examinee is examined by the examination apparatus installed in an examination room. In many cases a physician and a laboratory technician who operates the examination apparatus are different individuals. Because of this, medical mistakes may occur, such as the examinee going to an incorrect examination apparatus, or the laboratory technician making a mistake as to the examinee's identity and performing examination on the wrong examinee.

To prevent such medical mistakes, Japanese Patent Application Laid-Open No. 2002-222256 discloses a medical system which stores data and fingerprint data unique to the examinee on a server, and confirms the identity of the examinee before examination by performing fingerprint authentication, so as to prevent such a medical mistake as patient identification error. Japanese Patent Application Laid-Open No. 2002-336268 discloses a surgical system in which the patient wears a wristband, and the operation of the medical equipment is controlled based on the information from a unit that reads the information stored in the wristband.

Patent Literature 1: Japanese Patent Application Laid-Open No. 2002-222256
Patent Literature 2: Japanese Patent Application Laid-Open No. 2002-336268

SUMMARY OF THE INVENTION

In the medical system according to Japanese Patent Application Laid-Open No. 2002-222256, the fingerprint data for personal authentication is stored on the server, and the server is connected to a network. This authentication of a patient is performed by collating the fingerprint data stored on the server and the fingerprint data of the patient acquired by a fingerprint reading apparatus. As a result, such a medical mistake as patient identification error can be prevented. On the other hand, since it is possible that fingerprint data, to identify the individual, can be leaked, therefore server security must be strictly managed.

In the case of the method of confirming an examinee by a wristband, disclosed in Japanese Patent Application Laid-Open No. 2002-336268, an advantage is that, since the examinee is confirmed using a wristband, the personal information to identify the individual, such as fingerprint data, does not leak. Another advantage is that the wristband itself has low cost. However if the wristband is switched with another examinee intentionally or by mistake, the individual who is not the examinee may be identified as the actual examinee, in other words, a patient identification error may occur.

With the foregoing in view, it is an object of the present invention to provide a medical examination system that prevents examinee identification error, and prevents a leak of personal information of an examinee.

The present invention provides an examination system comprising a mobile apparatus and an examination apparatus, the mobile apparatus including:
a biological object information storing unit configured to store biological object information of an examinee;
a reading unit configured to read biological object information of the examinee;
a comparing unit configured to compare the biological object information read by the reading unit, and the biological object information stored in the biological object information storing unit; and
an outputting unit configured to output a result of the biological object information comparison by the comparing unit, the examination apparatus including:
an examination information acquiring unit configured to acquire examination information, which is information on examination performed on the examinee by the examination apparatus; and
a controlling unit configured to control the operation of the examination apparatus based on the result of the biological object information comparison output by the outputting unit, and the examination information.

The present invention provides a mobile apparatus which is used for performing examination using an examination apparatus, comprising:
a biological object information storing unit configured to store biological object information of an examinee in advance;
a reading unit configured to read biological object information of the examinee,
a comparing unit configured to compare the biological object information read by the reading unit, and the biological object information stored in the biological object information storing unit; and
an outputting unit configured to output a result of the biological object information comparison.

The present invention provides an examination method comprising the steps of:
reading biological object information of an examinee;
comparing the biological object information read in the reading step, and biological object information stored in a biological object information storing unit of a mobile apparatus;
outputting a result of the biological object information comparison;
acquiring examination information which is information on the examination performed on the examinee by the examination apparatus; and
controlling operation of the examination apparatus based on the comparison result in the comparing step, and the examination information.

The present invention can provide a medical examination system that prevents examinee identification error, and prevents the leak of personal identification information of an examinee.

Further features of the present invention will become apparent from the following description of exemplary embodiments with reference to the attached drawings.

DESCRIPTION OF THE EMBODIMENTS

Embodiments of the present invention will now be described with reference to the drawings. Dimensions, materials, shapes and relative positions of the components described below can be appropriately changed depending on the configuration and various conditions of the apparatus to which the present invention is applied. Therefore the scope of the invention is not limited to the following description.

The present invention is applied to a medical system that includes an examination apparatus. An examinee herein can be a patient, an examinee for a medical checkup or the like. The examination apparatus of the present invention is, for example, a photoacoustic imaging apparatus, an ultrasonic imaging apparatus, an X-ray imaging apparatus, a CT apparatus, an MRI apparatus or a retinal camera. The examination apparatus is not limited to these apparatuses. In some cases, one examination apparatus can execute a plurality of types of examinations, such as a composite apparatus that performs photoacoustic measurement and ultrasonic measurement. The present invention prevents the generation of medical mistakes, such as examinee identification error, when the examination apparatus is used. Furthermore, the present invention has a high security holding function for personal information of an examinee.

(Photoacoustic Imaging Apparatus)

Before describing embodiments of the present invention in detail, a photoacoustic imaging apparatus, which is an example of an examination apparatus, will be described. In concrete terms, a configuration of a photoacoustic imaging apparatus suitable for observing a breast will be described. Application of the present invention, however, is not limited to a photoacoustic imaging apparatus. The present invention can be applied to a medical system equipped with a plurality of examination apparatuses as well.

Figure 6:
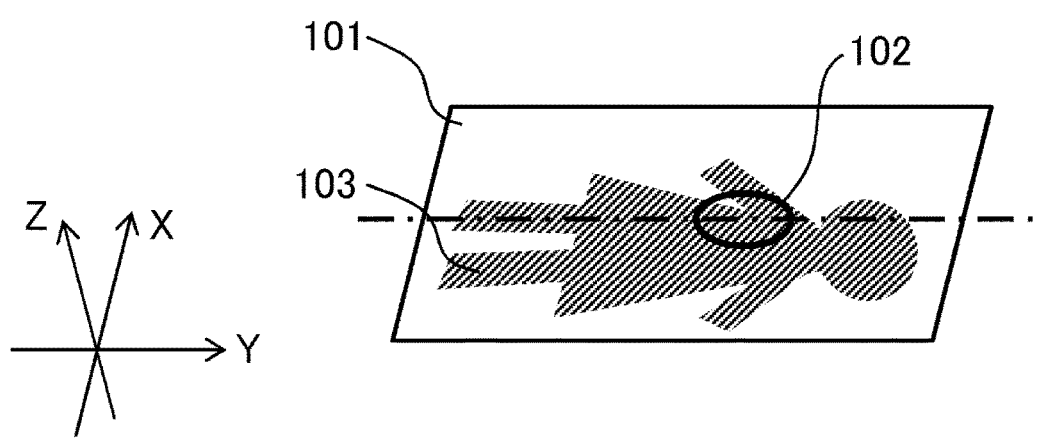
FIG. 6 is a schematic diagram depicting an examination table and state of a patient.

FIG. 6 is a schematic diagram depicting an examination table of the photoacoustic imaging apparatus and a position of a patient during examination. In FIG. 6, it is assumed that the X axis is the left-right direction, the Y axis is the head-tail direction, and the Z axis is the ventrodorsal direction of the patient. Reference sign 101 denotes an examination table, 102 denotes an examination window disposed in the examination table 101, and 103 denotes the position of the patient on the examination table.

For example, if the left breast of the patient is examined, the patient lies face down on the examination table 101 so that the body of the patient is in the position denoted by 103. Then the patient lies down in the position shifted to the right (when viewed from the patient) from the center of the examination table 101. As a result, the left breast can be inserted into the examination window 102. To examine the right breast, on the other hand, the patient lies face down in a position shifted to the left from the center of the examination table 101.

An irradiation unit configured to irradiate light from a light source (e.g. a pulse laser) and a support on which a receiving element (e.g. a piezoelectric element) configured to convert an acoustic wave into an electric signal are disposed inside the examination window 102. Various optical members, such as a bundle fiber, a mirror, a prism and a diffusion plate can be used for the irradiation unit. A scanning mechanism (e.g. XY stage), to measure a wide range by moving the support on the XY plane (horizontal direction) with respect to the object, may be included. The photoacoustic imaging apparatus also includes an information processing unit configured to acquire characteristic information (e.g. initial sound pressure distribution, absorption coefficient distribution, oxygen saturation distribution) inside the object by image reconstruction processing using the electric signal. For the information processing unit, an image processing apparatus (e.g. a PC, a workstation) including operation resources (e.g. a processor, a memory), which operate according to a program instruction is preferable.

When the irradiation unit irradiates light onto the breast, an acoustic wave (photoacoustic wave) is generated by the photoacoustic effect. The receiving element receives the photoacoustic wave and converts it into an electric signal. The characteristic information is acquired by the information processing unit reconstructing an image based on the electric signal and light intensity.

Embodiment 1

(System configuration)

Figure 2A:
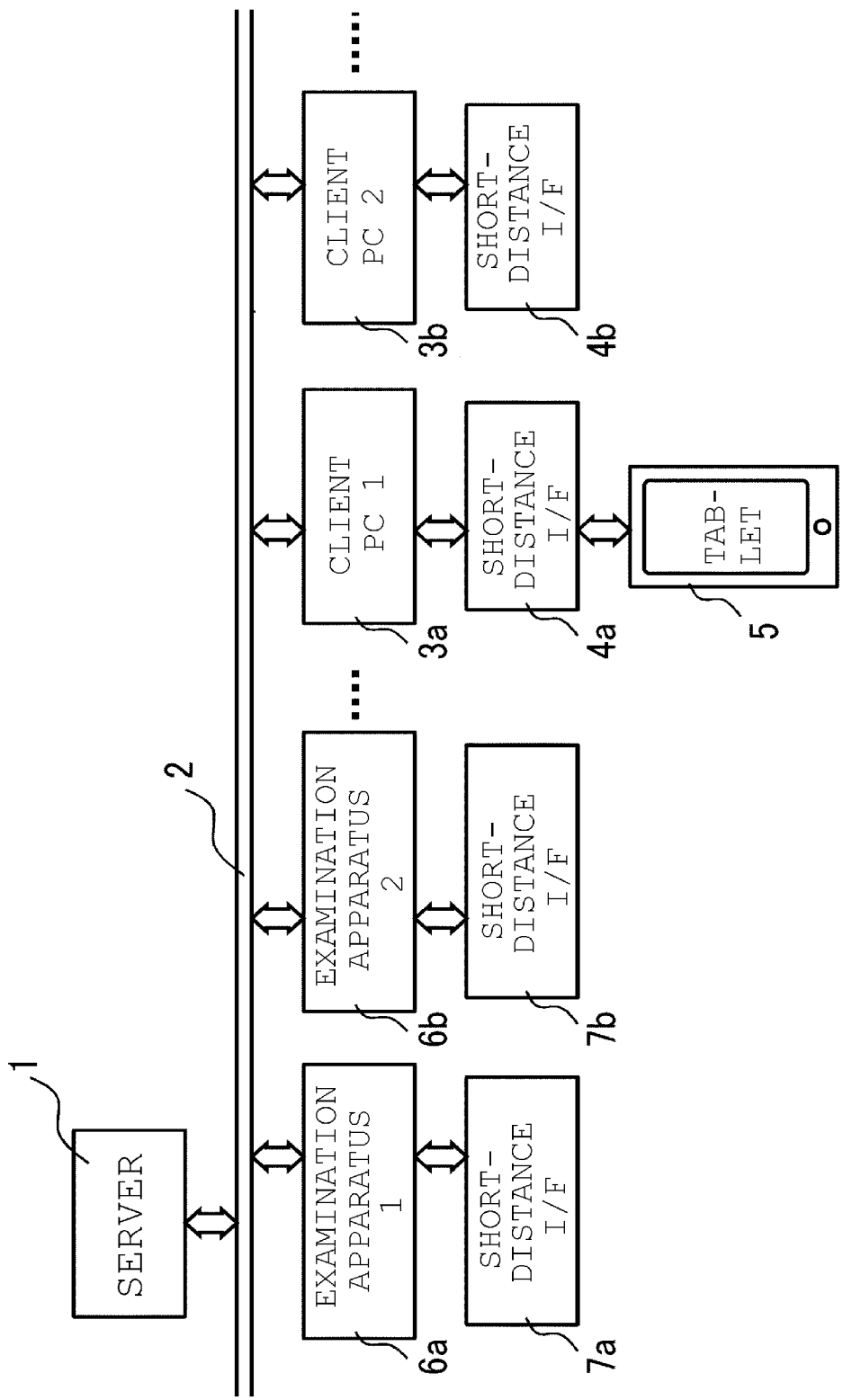
FIG. 2A is a block diagram of the medical system according to an embodiment of the present invention.
Figure 2B:
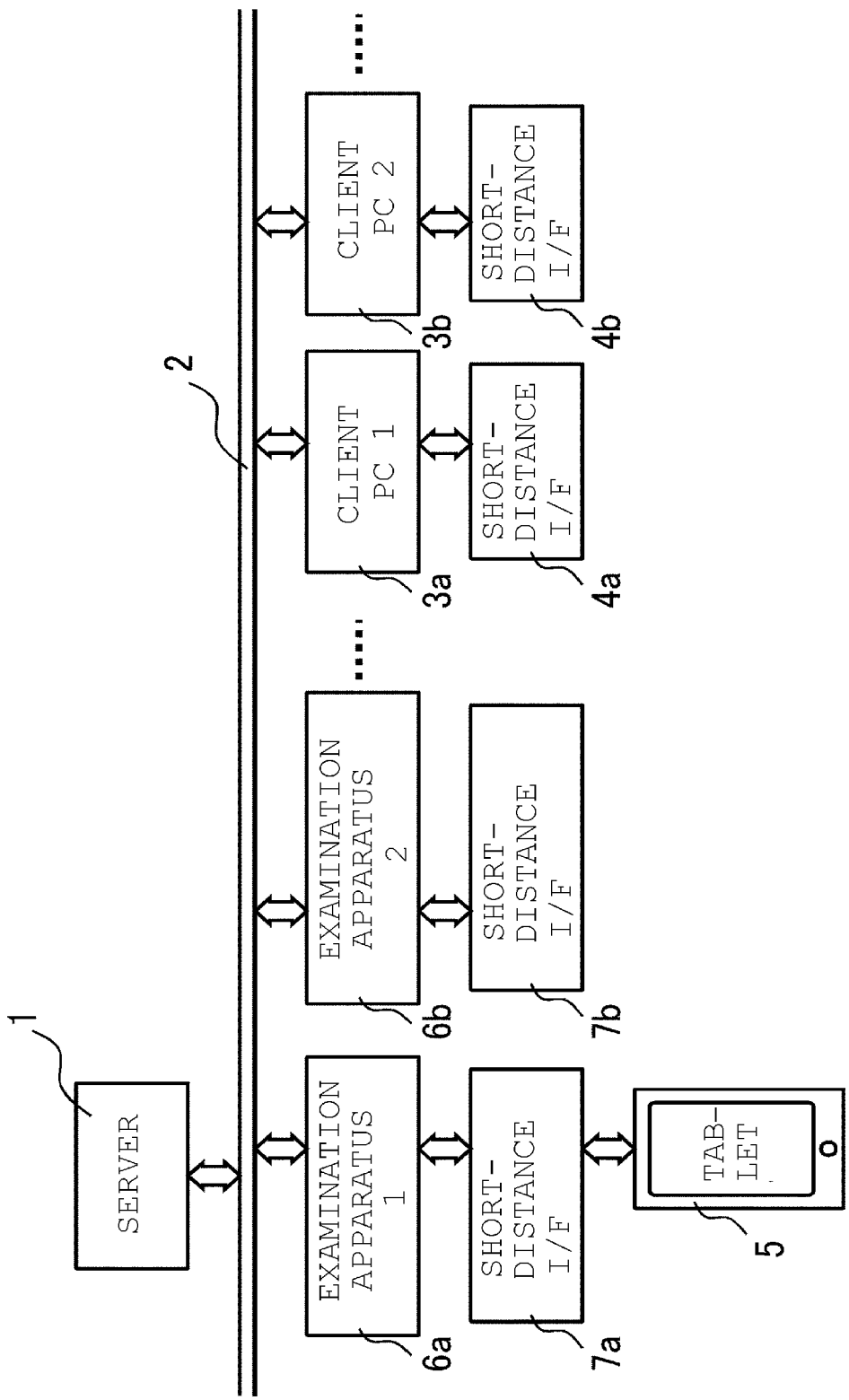
FIG. 2B is another block diagram of the medical system according to an embodiment of the present invention.

FIGS. 2A and 2B are block diagrams of a medical examination system according to an embodiment of the present invention. A reference sign 1 denotes a server, and 2 denotes a network. Reference signs 3a and 3b denote client PCs, which are permanently installed in an examination room of each physician, for example. Reference signs 4a and 4b denote short-distance I/Fs which are: cable interfaces, short-distance wireless communications called "NFCs", optical communications or the like. When a tablet PC is disposed in a later mentioned holder, a connection is established, and communication via the short-distance I/F is enabled.

A reference sign 5 denotes a tablet PC which has a communication function with the short-distance I/F and a biological object authentication function. In this description, a slate type tablet PC is used as an example. However, a portable type compact PC, a wearable PC, a mobile telephone referred to as a smartphone, a portable music player or the like may be used. Any apparatus having the later mentioned functions can be used as a mobile apparatus of the present invention.

In addition to the information storing function, the information processing function, the communicating function and the information outputting function of a standard mobile information apparatus (mobile information terminal), the mobile apparatus of the present invention includes a biological object information reading unit configured to read biological object information of an examinee. If the biological object information is a fingerprint, any fingerprint reader, such as an optical type or semiconductor type, can be used as the biological object information reading unit. The biological object information reading unit corresponds to the reading unit of the present invention. Each function of the mobile apparatus is implemented using operation resources, such as a CPU, a memory and a communication mechanism which operate according to programs. The memory can be used as the biological object information storing unit or the examination information storing unit of the present invention. The functions of the comparing unit and the comparison result outputting unit of the present invention can be implemented as an operation of each block according to a predetermined program.

Reference signs 6a and 6b denote examination apparatuses which are selected from the above mentioned various medical examination apparatuses in accordance with the diagnostic result by a physician or the items of a physical check list. The examination apparatus encloses a computer, or is connected to a computer. The computer includes such operation resources as a CPU, a memory and a communication mechanism, and has such functions as operation control of the apparatus, data processing, information storage and network connection. The computer of the examination apparatus functions as the operation controlling unit and examination information acquiring unit of the present invention. The examination information acquiring method, in the case when the computer of the examination apparatus functions as the examination information acquiring unit, varies. For example, a method of acquiring the examination information from the server, using the information to specify the tablet PC or examinee as a key, a method of acquiring the examination information from the examination information storing unit of the tablet PC, a method of acquiring the examination information via UI or the like, can be used.

A concrete example of the case when the examination apparatus is a photoacoustic imaging apparatus, which includes a light source and a receiving element configured to receive an acoustic wave which is generated from an examinee in response to light irradiation from the light source, will be described. For the light source, a pulse laser apparatus is preferable. A flash lamp, a light emitting diode or the like can also be used. If a light source which can irradiate light having a plurality of wavelengths is used, a concentration ratio of substances constituting the biological object (e.g. oxygen saturation) can be acquired. The receiving element receives a photoacoustic wave generated from an object, to which the laser light was irradiated, and converts the photoacoustic wave into an electric signal. For example, a piezoelectric element, a Fabry-Perot interferometer, a capacitive micro-machined ultrasonic transducer (CMUT) or the like can be used. The apparatus includes a signal processing unit constituted by circuits to amplify electric signals and perform digital conversion. The apparatus also includes such operation resources as a CPU and a memory, and an information processing unit that operates according to programs. The information processing unit acquires characteristic information by image reconstruction using electric signals (e.g. via a phasing addition method, a Fourier transform method).

Reference signs 7a and 7b are short-distance I/Fs. In FIG. 2, 2 client PCs and 2 examination apparatuses are illustrated. The number of units can be changed depending on the scale of the hospital or examination facility, the state of the examinee, the diagnostic content by the physician, a number of examination items on the physical checkup list and the like.

(Outline of Examination)

In FIG. 2A, the physician checks the patient, connects the tablet PC 5 to the client PC 3a via the short-distance I/F 4a, determines the examination content of the patient, and stores this content in the tablet PC 5 and server 1 as the examination information. The examination information stored in the server 1 includes the information to specify the tablet PC 5 or the patient identity, in addition to the examination content. The physician also stores the biological object information, which is used for biological object authentication to confirm patient identity to the tablet PC 5. For the biological object authentication, a fingerprint, iris, retina, blood vessel (e.g. vein), handprint, face, voice print or the like can be used. In this embodiment, a fingerprint, which is widely used, will be described as an example of the biological object authentication. The biological object information in this case is information on the fingerprint.

In the case of an examination on a healthy individual, such as a physical checkup, the examinee is not called a patient, but in this description, the term "patient" is used to include a healthy individual. Further, the individual who specifies the examination items in the physical checkup or the like is not always a physician, but in this description, the term "physician" is used. The patient holding the tablet PC 5 enters the room where the examination apparatus 6a is installed, and sets the tablet PC 5 in the holder of the examination apparatus 6a. It is preferable that the tablet PC 5 provides guidance to the patient by sound or image regarding the way to the examination room, and setting the tablet PC 5 in the holder.

The system configuration, after the patient sets the tablet PC 5 in the holder of the examination apparatus 6a, will be described with reference to FIG. 2B. When the patient sets the tablet PC 5 in the holder and communication between the tablet PC and examination apparatus 6a is established, the tablet PC 5 and examination apparatus 6a start communication via the short-distance I/F 7a. Then, as described above, the examination information stored in the tablet PC 5 and the examination information stored on the server are collated. In this case, it is preferable that the tablet PC 5 requests, by display or sound, authentication to the patient at the point when the communication between the tablet PC 5 and the examination apparatus 6a is established. This request may be performed at the point when the communication between the tablet PC 5 and the examination apparatus 6a is established, and the examinee is settled in the examination position. The patient is positioned with respect to the examination apparatus to receive examination, and the patient performs fingerprint authentication in this state using the tablet PC.

Figure 1A:
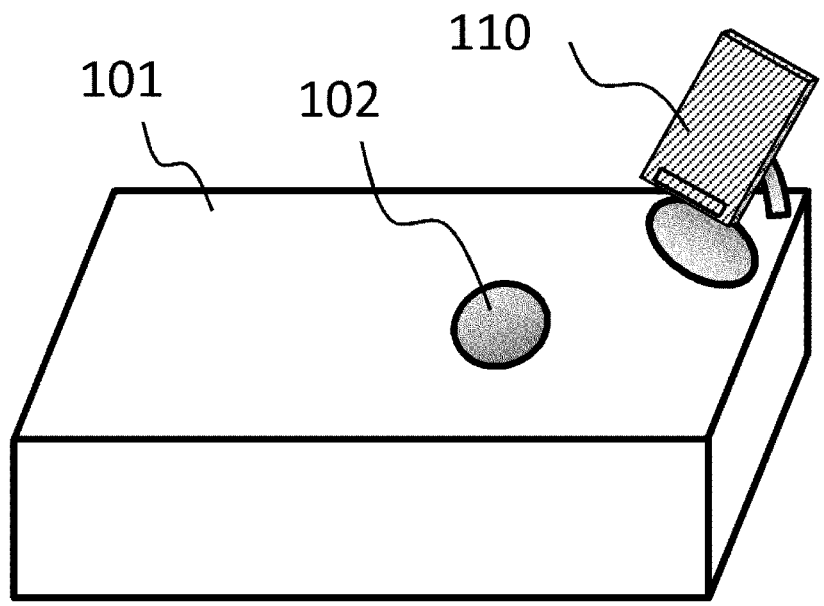
FIGS. 1A and 1B are schematic diagrams of an examination apparatus that is suitable for a medical system according to an embodiment of the present invention.

FIG. 1 illustrates the configuration of the specific examination apparatus 6a (in this embodiment, the photoacoustic imaging apparatus used to examine a breast). In FIG. 1A, the reference sign 101 denotes the examination table of the examination apparatus 6a. The reference sign 102 denotes the detection window created in the examination table 101, and is used to insert the breast of the patient. The reference sign 110 denotes a holder in which the tablet PC 5 is set, that is, a holding unit configured to hold the tablet PC 5. In the holder 110, the short-distance I/F 7a, which is the short-distance communicating unit, is included (not illustrated). The holding unit can be configured using any material, such as plastic and metal, as long as the terminal can be held. A mounting unit, which can change the holding unit in accordance with the type of terminal, may be disposed.

Figure 1B:
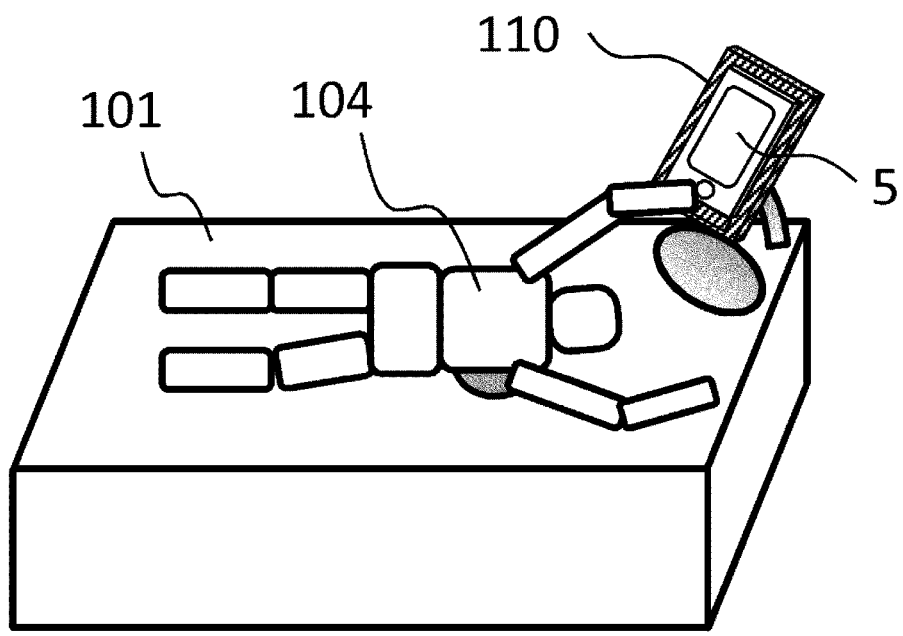

In FIG. 1B, the patient denoted by the reference sign 104 lies face down on the examination table, and one breast is inserted into the examination window 102. Only when the tablet PC 5 is set in the holder, the communication between the tablet PC 5 and the examination apparatus 6a is established via the short-distance I/F 7a. The short-distance I/F 7a is implemented by cable communication such as USB, or short-distance wireless communication such as NFC, or optical communication such as infrared.

When the communication between the tablet PC 5 and the examination apparatus 6a is established via the short-distance I/F 7a, the examination information is collated to confirm whether the examination content is correct. At the same time, the biological object authentication by the tablet PC 5 becomes possible, and the patient contacts their finger to the biological object information reading unit according to the guidance by the tablet PC 5. The tablet PC 5 reads the finger print as the biological object information, and compares the fingerprint with the fingerprint of the patient stored in advance. If the comparison result shows that these fingerprints are from the same individual, the personal authentication completes. The result of the personal authentication (affirmative or negative) is output to the examination apparatus 6a. The examination apparatus 6a starts the examination when the examination content is correct and the personal authentication is completed.

The tablet PC 5 may externally notify whether the result of the personal authentication is affirmative or negative by sound or image. When this occurs, the laboratory technician who recognizes the result of the notified personal authentication begins the examination. A display or a speaker included in the tablet PC 5 constitutes a notification unit that notifies the authentication result. The notification unit may be an apparatus having a configuration that is different from the configuration included in the tablet PC. Any member using a conventional communication technique, such as a combination of a communication chip and antenna, can be used for the notification unit.

In the present invention, the patient is authenticated by sending only the biological object information authentication result acquired by the tablet PC 5 to the examination apparatus 6a via the short-distance I/F 7a. Therefore in the present invention, the biological object information, such as the fingerprint information, to identify the patient, is never stored on the server 1, therefore high information security is maintained. In other words, according to the present invention, the biological object information is stored in the tablet PC 5, and only the authentication result is sent to the examination apparatus 6a which is connected to the network 2. Furthermore, the tablet PC 5 is normally not connected to a network. If the biological object information, such as fingerprint information, is deleted after the examination is over, the information security is heightened.

It is preferable that the holder 110 is installed at a position where the biological object authentication, such as fingerprint authentication, can be easily performed in a state where the patient can be examined. It is preferable that the holder 110 is installed at a position whereby the fingerprint authentication is easily performed when the patient 104 lies face down with a breast inserted in the examination window 102. In the photoacoustic imaging apparatus illustrated in FIG. 1, it is preferable that the position of the holder 110 is moved manually or automatically by a moving mechanism. The examination apparatus 6a can acquire in advance examination information (e.g. examining the left breast) from the server 1. According to this examination information, the position of the holder 110 on the examination table 101 is changed.

Information on which hand (left or right) is used for the fingerprint authentication may be stored in the examination room together with the acquired fingerprint information, and the information on which hand is used may be sent to the server 1 in advance. Thereby, the holder 110 of the examination apparatus 6a can be moved to an appropriate position. As a result, the patient can be prevented from performing the fingerprint authentication in an unnatural posture.

(Processing Flow)

Figure 3:
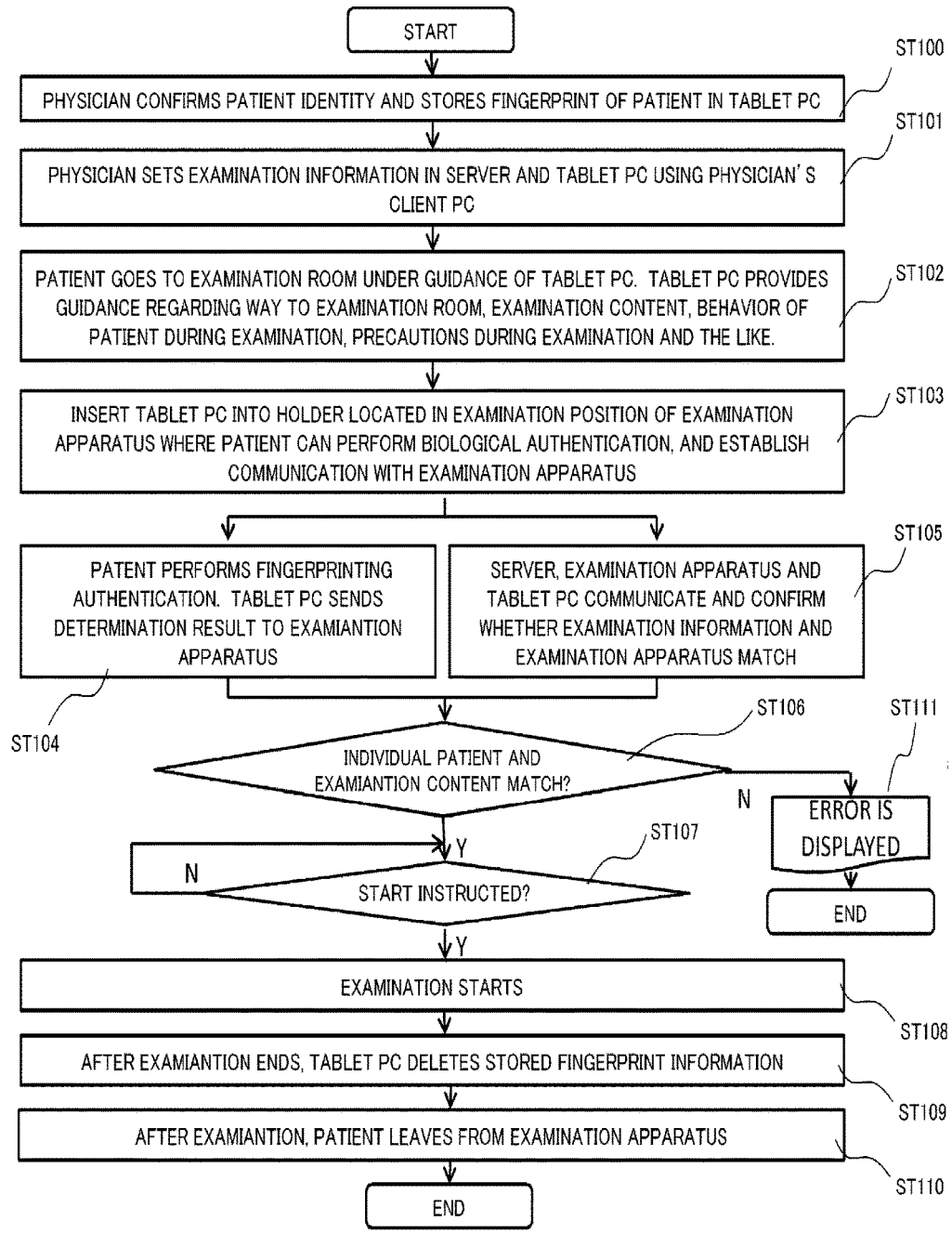
FIG. 3 is a flow chart of Embodiment 1.

The processing flow of this embodiment will be described in detail with reference to FIG. 3. A physician who sets the examination information, a patient who is the examinee, and a technician who operates the examination apparatus are involved in this processing flow. Firstly, the physician explains the examination content to the patient who came to the examination room to receive examination, hands the tablet PC 5 over to the patient, and stores the fingerprint of the patient in the memory of the tablet PC 5 after confirming the patient identity (step ST100). Then the physician sets the examination information in the server 1 and the tablet PC 5 using the client PC 3a (step ST101). In step ST101, the physician may set the examination information in the tablet PC 5 in advance, without using the client PC 5.

The examination information includes the type of examination, examination apparatus installation location, examination apparatus name, examination area, examination apparatus parameters, examination conditions (e.g. blood pressure, pulse) of the patient and the like. If the examination apparatus can execute a plurality of types of examinations, the examination information includes the information on which type of examination is executed. If the examination information is set in the server 1, information to specify the tablet PC 5 or the patient is included. In step ST100 and ST101, the tablet PC 5 is connected to the client PC 3a via the short-distance I/F 4a. The short-distance I/Fs 4a and 4b are used when the physician inputs the fingerprint information and the like while speaking with the patient, hence unlike the short-distance I/Fs 7a and 7b of the examination apparatuses, the short-distance I/Fs 4a and 4b need not be I/Fs which can communicate only when the tablet PC 5 is inserted in the holder. For example, the short-distance I/Fs 4a and 4b may be I/Fs conforming to the short-distance wireless communication standard, such as Bluetooth, or to the wireless LAN standard, such as Wi-Fi.

Then the patient carries the tablet PC 5 and goes to the examination room adhering to the guidance provided by the tablet PC 5. The tablet PC 5 provides at least one guidance regarding the way to the examination room, the examination content, the behavior of a patient during examination, and the precautions during examination (step ST102). If guidance is unnecessary for the examination, guidance need not be provided. It is also possible to add a condition such that biological object authentication is enabled after the guidance is over. This added condition is preferable since the patient will go through the guidance with certainty.

The patient who comes to the examination room inserts the tablet PC 5 in the holder 110 of the examination apparatus 6a adhering to the guidance. The tablet PC 5, that is set in the holder, establishes communication with the examination apparatus 6a (step ST103).

Then the patient performs fingerprint authentication. In other words, the stored fingerprint information and the actually measured fingerprint information are compared, and it is determined whether the authentication result is affirmative or negative. The tablet PC 5 sends the determination result to the examination apparatus 6a. At this time, the fingerprint information, which is the personal biological object information, remains in the tablet PC memory (step ST104). As mentioned above, it is preferable to execute this step after the guidance is over.

At the same time, the server 1, the examination apparatus 6a and the tablet PC 5 communicate to confirm whether the examination information and the examination apparatus match (step ST105). Prior to this step, it is preferable that the examination apparatus 6*a* acquires the examination information. Steps ST104 and ST105 need not be executed in parallel. For example, step ST105 is executed first, and then the fingerprint authentication is requested to the patient by display or sound, and then step S104 is executed.

In step ST106, the results of steps ST104 and ST105 are determined by the computer of the examination apparatus or by the controlling unit. In other words, if the result of the fingerprint authentication is affirmative and the examination information and the examination apparatus match, it is determined that the patient and the examination content are correct.

If at least either one of the fingerprint information and the examination information is incorrect, an error message, to indicate that the patient or the examination information is incorrect, is displayed on the examination apparatus 6*a* or on the tablet PC 5, and processing ends (step ST111). It is also preferable to disable the execution of the examination by feeding back the information that the result of the personal authentication is negative to the examination apparatus. For example, a method of disabling input of the examination start instruction or a method of locking the apparatus can be used. Acquiring the examination information from the server is not essential. For example, the technician may confirm the examination content. In this case, it is determined whether the examination can be executed or not based on the comparison result between the stored fingerprint and the actually read fingerprint.

If both the fingerprint information and the examination information are correct, the examination apparatus waits for the examination start instruction (step ST107). When the examination start instruction is received, the examination apparatus starts examination (step ST108). The examination start instruction is executed by the laboratory technician moving a cursor to the START icon displayed on the monitor of the examination apparatus 6*a*, and clicking the mouse button, for example. Depending on the examination content, the examination apparatus may automatically start the examination if the personal authentication result is affirmative and execution of the examination is possible.

In the case of receiving examination on both breasts, the patient receives measurement of one breast, then adhering to the guidance of the tablet PC 5, inserts the other breast into the examination window 102, and processing is repeated from step ST107. Since examination information is stored in the tablet PC 5 in advance, such guidance becomes possible. During the examination, the tablet PC notifies the patient, via sound or image, on the examination progress state for the examination area, the remaining time of examination and the like. In the case of the photoacoustic imaging apparatus, the patient wears protective glasses because a high power pulse laser is used. Therefore a sound alert is preferable for the guidance to the patient. For the type of the biological object authentication, a fingerprint is preferable, rather than an iris, retina, face or the like, since the patient is wearing protective glasses. For the same reason, a fingerprint is also preferable for the biological object authentication in an ophthalmological examination, such as an examination using a retinal camera.

When the examination is over, the examination apparatus 6*a* notifies the tablet PC 5 that the examination ended. Then the tablet PC 5 deletes the stored fingerprint information (step ST109). Then the examination apparatus 6*a* notifies the patient that the examination ended by a display on, or sound from, the tablet PC 5. Then the patient leaves the examination table 101 (step ST110). The examination ends when the above steps complete.

In the description of this embodiment, it is assumed that the hospital provides the tablet PC. However a mobile apparatus, such as a smartphone owned by the patient, may be used. In this case, it is preferable that an application corresponding to the examination system is installed on the smartphone in advance. In the case of using a smartphone owned by the patient, the biological object information (e.g. fingerprint information) need not be deleted after the examination ends.

According to this embodiment, a patient identification error can be prevented in the medical examination. Particularly, even if a tablet PC is switched between patients intentionally or by mistake, a patient identification error can be prevented because of the biological object authentication function of the tablet PC. Further, the patient receiving an incorrect examination by an examination apparatus that a physician did not specify can be prevented. Furthermore, the biological object information to specify an individual identity is not stored on a server or client PC connected to a network, hence high information security can be maintained. Moreover, by providing a tablet PC which provides the patient with guidance and assistance during the examination, patient apprehension about the examination can be appeased.

Embodiment 2

Figure 4:
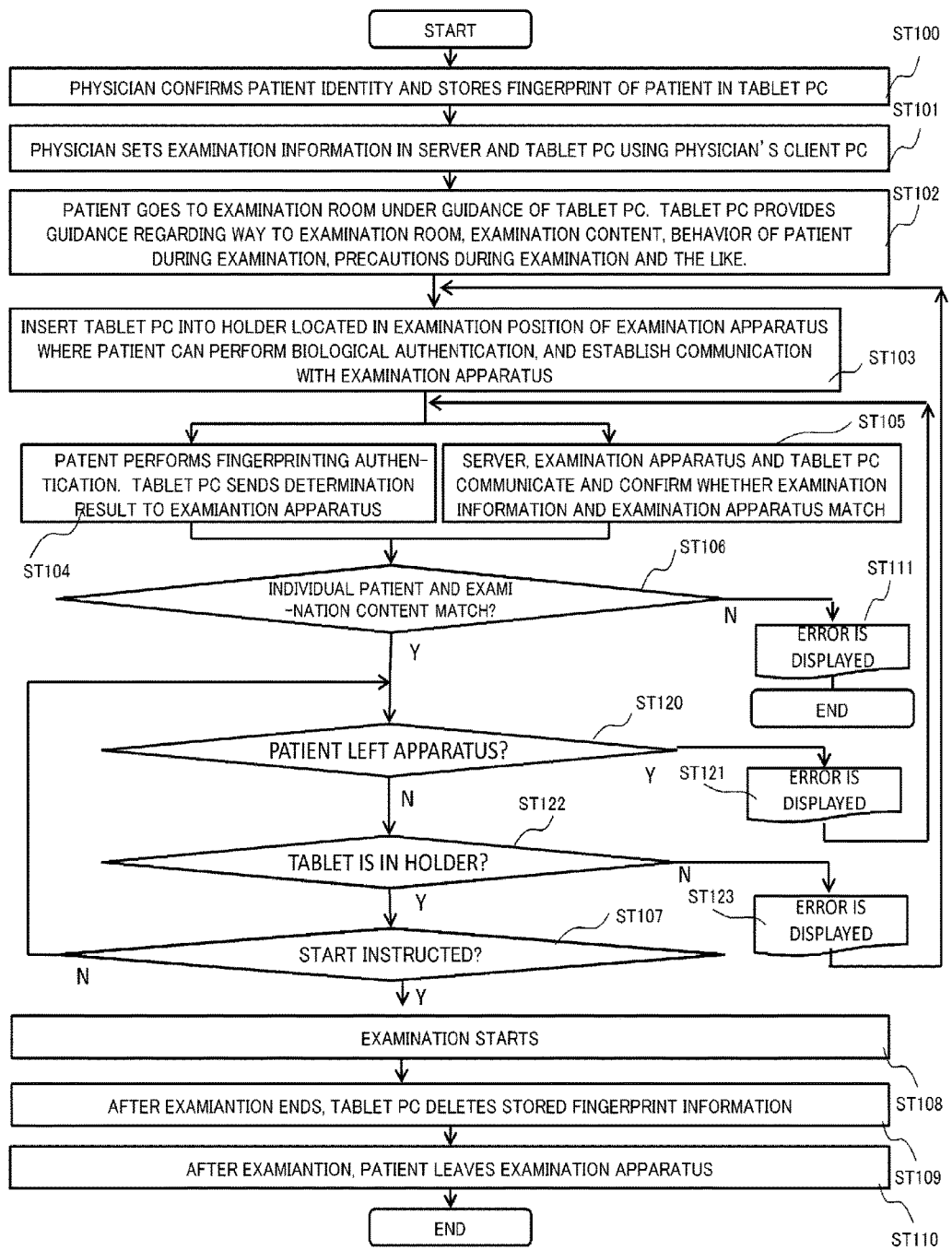
FIG. 4 is a flow chart of Embodiment 2.

In Embodiment 2, the patient identification error caused by switching patients immediately prior to the examination is prevented. The processing flow of Embodiment 2 will be described focusing on the differences from Embodiment 1 with reference to FIG. 4.

The processing in steps ST100 to ST102 are performed in the same way as Embodiment 1. Thereby, the steps of storing the fingerprint information to the tablet PC 5 (ST100), setting the examination information in the server 1 and the tablet PC 5 (ST101), and moving the patient adhering to the guidance provided by the tablet PC 5 (ST102) are completed. Furthermore, the processing in steps ST103 to ST106 and ST111 are also performed in the same way as Embodiment 1. Thereby, the steps of installing the tablet PC 5 (ST103), performing the biological object authentication (ST104), confirming the examination apparatus (ST105), determining whether the examination can be performed (ST106), and performing exception handling when the determination result is negative (ST111) are completed.

A difference from Embodiment 1 is, when the determination result is affirmative (step ST106=Y), it is confirmed that the patient did not leave the examination apparatus (step ST120) and that the tablet PC is set in the holder (step ST 122) while waiting for an instruction to start the examination. If the patient has left the examination apparatus, notification that the patient has left the examination apparatus is displayed (step ST121), and processing returns to steps ST104 and ST105. If the tablet PC 5 is not set in the holder, notification that the tablet PC is not set in the holder is displayed (step ST123), and processing returns to step ST103.

If the patient did not leave the examination apparatus and the tablet PC is set in the holder, the examination can be performed without patient identification error, hence the examination starts when the examination start instruction is received (steps ST107, ST108). The processing of steps ST109 and ST110 after the examination ended are the same as Embodiment 1.

The means of confirming that the patient did not leave a predetermined measurement position of the examination apparatus in step ST120 will be described. In the photoacoustic imaging apparatus, it is preferable that a load indicator is installed in the examination table 101. By monitoring the weight applied to the examination table using the load indicator, it can be determined that the patient has left the examination apparatus when the weight is decreased. Another method is measuring the distance between the examination apparatus and the patient by image recognition using an external camera, whereby it is determined that the patient has left the examination apparatus when the distance increased. In the case of a retinal camera, the distance between the patient and the examination apparatus may be measured by an electrostatic capacitance sensor, an ultrasonic sensor or the like, whereby it is determined that the patient has left the examination apparatus when a predetermined distance is exceeded. These means can be used as the examination target confirming unit of the present invention.

A means of detecting whether the tablet PC 5 is set in the holder in step ST122 will be described. One available method is disposing a switch inside the holder, and determining the presence of the tablet PC 5 by the ON/OFF state of the switch. For the switch, a micro switch can be used, for example. It is preferable that the push button or lever of the switch is automatically pressed when the tablet PC 5 is set in the holder. It may be determined whether the tablet PC 5 is set in the holder by connection/disconnection of the communication via the short-distance I/F 7a. An optical sensor, a weight sensor or the like can also be used. These means can be used as the mobile apparatus confirming unit of the present invention.

As described above, according to Embodiment 2, not only can the effects described in Embodiment 1 be implemented, but the patient identification error as well can be prevented even if patients are switched intentionally or by mistake after the patient is positioned at the examination apparatus and fingerprint authentication is performed.

Embodiment 3

Figure 5:
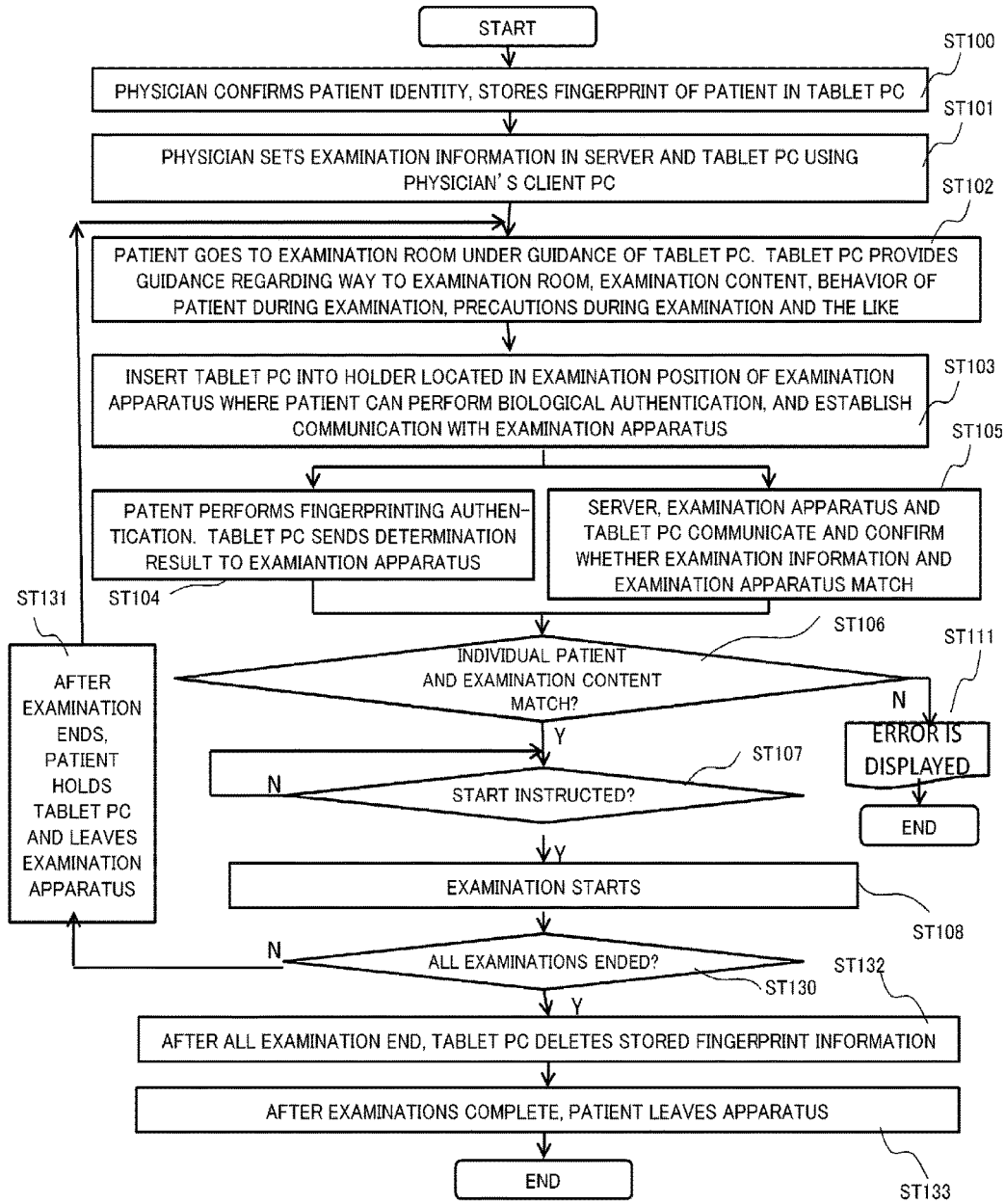
FIG. 5 is a flow chart of Embodiment 3.

In Embodiment 3, one patient receives a plurality of examinations. Particularly in a physical examination, such as a clinical survey examination, normally a plurality of types of examination items are performed. Embodiment 3 will now be described with reference to FIG. 5 focusing on the differences from Embodiments 1 and 2.

The processing in steps ST100 to ST102 are performed in the same way as Embodiment 1. Thereby, the steps of storing the fingerprint information in the tablet PC 5 (ST100), setting the examination information in the server 1 and the tablet PC 5 (ST101), and moving the patient adhering to the guidance provided by the tablet PC 5 (step ST102) are completed. The examination information here includes a plurality of types of examination items. The tablet PC 5 guides the patient according to the sequence of the examinations that are set. It is preferable that the sequence of the examinations is determined in accordance with the degree of stress on the patient in each examination item and the working status of the examination apparatus.

The processing in steps ST103 to ST106 and ST111 are also performed in the same way as Embodiment 1. Thereby, the steps of setting the tablet PC 5 (ST103), performing biological object authentication (ST104), confirming the examination apparatus (ST105), determining whether the examination can be executed (ST106), and performing exception handling when the determination result is negative (ST111) are completed. In Embodiment 3, if the determination result is affirmative (examination apparatus and examination information matches and authentication result is correct), the start instruction is confirmed, and the examination is performed similarly to Embodiment 1 (steps ST107 and ST108).

When the examination ends, the examination apparatus 6a notifies the end of the examination to the tablet PC 5 via the short-distance I/F 7a. The tablet PC 5 notifies the patient that the examination by this examination apparatus ends by display or sound. Then the tablet PC 5 determines whether all examinations ended based on the examination information stored in advance and the examination end information acquired from the examination apparatus 6a (step ST130). If not all examinations are ended, the tablet PC notifies the next examination content to the patient by sound or display. At this time, it is preferable to instruct the patient to hold the tablet PC and leave the examination table 101. Adhering to the instruction, the patient holds the tablet PC and leaves the examination table 101 (step ST131).

Processing returns to step ST102. The tablet PC provides guidance regarding the next examination apparatus and guides the patient to the examination room. In the case of performing a plurality of examinations, it is preferable to display a total number of examination items, a number of completed examination items, or a % of the examinations which are completed. In the present invention where the same tablet PC 5 is used, this guidance is easily performed even when a plurality of examinations are performed. Then steps ST103 to ST108 are performed, and processing returns to step ST130. If the tablet PC determines that all the examinations are ended in step ST130, processing advances to step ST132.

In step ST132, the tablet PC 5 deletes the stored fingerprint information, and notifies the completion of all the examinations to the patient by sound or display. Then in step ST133, the patient leaves the examination apparatus since the examinations ended. By the above steps, the examinations are completed.

Each step described in Embodiment 2 (steps ST120 to ST123) may be added to the processing in Embodiment 3. Then a patient identification error can be prevented even if the patients are switched intentionally or by mistake. The processing of Embodiment 3 can also be applied to the case when one examination apparatus has a plurality of examination functions.

As described above, the effects described in Embodiment 1 can also be implemented in Embodiment 3. Furthermore, even in the case when the patient receives a plurality of examinations by a plurality of examination apparatuses, the patient can be guided using the same tablet PC. Therefore the patient can always recognize the progress state of the examinations, and apprehension over the examinations can be appeased. Moreover, the biological object information, such as a fingerprint, is acquired only once even if a plurality of examinations are performed, hence high information security can be maintained.

Embodiment 4

In Embodiment 4, a case when the entire room, where the examination apparatus is installed, is regarded as an examination apparatus will be described. For example, in the case of such examination apparatuses as an X-ray imaging apparatus, CT apparatus and MRI apparatus, only the patient enters the examination room and receives examination in order to prevent radiation exposure to individuals other than the patient, or in order to improve measurement accuracy. In this case, the holder may be installed near the door of the entrance of the examination room. In this case, the biological object authentication is performed when the patient enters the room. Whether the examination information and the examination apparatus match is confirmed when the tablet PC is set in the holder. The configuration of installing the holder in such a position is also included within the scope of the present invention.

Particularly in such an examination apparatus as an MRI, the image quality of the MRI image may drop if the tablet PC is set near the examination apparatus. Moreover, the tablet PC may malfunction due to the strong magnetic field of the MRI. The present invention can be applied even in such a case by regarding the entire room where the examination apparatus is installed as the examination apparatus, as described in Embodiment 4.

According to Embodiment 4, the effects described in each of Embodiment 1 to 3 can be implemented even if it is difficult to carry the tablet PC into the examination room where the examination apparatus is installed, as described above. The configuration of Embodiment 4 can be applied to any of Embodiment 1 to 3.

Embodiment 5

As described in each of the above mentioned embodiments, the tablet PC receives input of the examination information, stores the fingerprint information, and provides guidance regarding the way to the examination room, examination content, behavior of the patient during the examination, and precautions during the examination. According to Embodiment 5, the physical conditions of the patient can be understood via the tablet PC providing guidance.

The method of understanding the physical conditions will be described in detail. Before performing the examination, the tablet PC confirms whether the patient can receive the examination based on the examination information. For example, if the examination is an X-ray of the stomach, it is confirmed that the patient has not eaten. For this confirmation, it is preferable to use a UI of the tablet PC 5, such as the display unit, speaker, touch panel and the like. If the patient is in a state that is inappropriate for the examination, the tablet PC 5 establishes communication with the examination apparatus 6a, and notifies the examination apparatus 6a that the patient is in a state that is inappropriate to be examined. Then the examination apparatus 6a cancels the examination.

For another operation example, the state of the patient is displayed on the display screen of the tablet PC 5, and instruction to hand the tablet PC 5 over to the laboratory technician is displayed. In this case, the laboratory technician who received the tablet PC 5 confirms with the patient on the details of the display content, and determines whether the examination can be performed or not.

Another example of understanding the state of the patient during guidance is linking with a wearable device which also communicates with the tablet PC 5. The wearable device can be a watch, wristband, spectacles or the like, and can acquire physical information including body temperature, pulse and blood pressure. The tablet PC 5 communicates with the wearable device and acquires the physical information of the patient. Then comparing the acquired physical information with the examination conditions, which was stored in the tablet PC 5 in advance, the tablet PC 5 determines whether the examination can be performed. The tablet PC 5 may guide the technician to confirm the physical information instead.

As described above, according to Embodiment 5, the tablet PC 5 or the wearable device understands the physical state of the patient. As a result, the examination can be cancelled if the physical state does not satisfy the examination conditions, and a risk of performing the examination on a patient who is in a poor physical state can be prevented.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-253188, filed on Dec. 25, 2015, which is hereby incorporated by reference herein in its entirety.

What is claimed is:

1. An examination system comprising a mobile apparatus and an examination apparatus, the mobile apparatus including a memory storing a program, and one or more processors which, by executing the program, function as:

a biological object information storing unit configured to store biological object information of an examinee;

a reading unit configured to read biological object information of the examinee;

a comparing unit configured to compare the biological object information read by the reading unit, and the biological object information stored in the biological object information storing unit in order to obtain a personal authentication result of the examinee using the respective biological object information; and an outputting unit configured to output the personal authentication result from the comparing unit to the examination apparatus via an interface, and the examination apparatus including a memory storing a program, and one or more processors which, by executing the program, function as:
an examination information acquiring unit configured to acquire examination information, which is information on an examination performed on the examinee by the examination apparatus; and
a controlling unit configured to control the operation of the examination apparatus based on the personal authentication result and the examination information.

2. The examination system according to claim 1, wherein the controlling unit enables execution of the examination when the personal authentication result is affirmative, and disables execution of the examination when the personal authentication result is negative.

3. The examination system according to claim 1, wherein the outputting unit allows a notification unit, included in the mobile apparatus, to issue a notification, by sound or image, on whether the personal authentication result is affirmative or negative.

4. The examination system according to claim 1, wherein the controlling unit starts the examination when the personal authentication result is affirmative.

5. The examination system according to claim 1, wherein the biological object information is a fingerprint of the examinee.

6. The examination system according to claim 1, wherein the examination information includes information on examination content of the examinee,
the mobile apparatus further includes an examination information storing unit configured to store the examination information,
the examination information acquiring unit acquires the examination information from the examination information storing unit, and
the controlling unit determines whether the examination content of the examinee matches the examination apparatus based on the examination information.

7. The examination system according to claim 1, wherein the examination information includes information on examination content of the examinee and information for specifying the examinee,
the examination information acquiring unit acquires the examination information from a server, and
the controlling unit determines whether the examination content of the examinee matches the examination apparatus based on the examination information.

8. The examination system according to claim 1, wherein the reading unit reads the biological object information after communication between the mobile apparatus and the examination apparatus is established.

9. The examination system according to claim 1, wherein the examination apparatus further includes a holding unit configured to hold the mobile apparatus, and
the reading unit reads the biological object information after the mobile apparatus is held by the holding unit.

10. The examination system according to claim 1, wherein the examination information acquiring unit acquires the examination information which a user sets up on a server.

11. The examination system according to claim 1, wherein the mobile apparatus provides guidance to the examinee regarding at least one of a way to the examination apparatus and a progress status of the examination being performed by the examination apparatus.

12. The examination system according to claim 1, wherein the mobile apparatus deletes the biological object information after the examination by the examination apparatus ends.

13. The examination system according to claim 1, wherein the examination apparatus further includes an examinee confirming unit configured to confirm whether the examinee has left a predetermined measurement position of the examination apparatus.

14. The examination system according to claim 9, wherein the examination apparatus further includes a mobile apparatus confirming unit configured to confirm whether the mobile apparatus is held by the holding unit.

15. The examination system according to claim 1, wherein the examination apparatus is a photoacoustic imaging apparatus which includes a light source and a receiving element configured to receive an acoustic wave which is generated from the examinee in response to light irradiated from the light source.

16. A mobile apparatus which is used for performing examination using an examination apparatus, comprising:
the mobile apparatus including a memory storing a program, and one or more processors which, by executing the program, function as:
a biological object information storing unit configured to store biological object information of an examinee in advance;
a reading unit configured to read biological object information of the examinee,
a comparing unit configured to compare the biological object information read by the reading unit, and the biological object information stored in the biological object information storing unit in order to obtain a personal authentication result of the examinee using the respective biological object information; and
an outputting unit configured to output the personal authentication result from the comparing unit to the examination apparatus via an interface.

17. An examination method comprising the steps of:
reading biological object information of an examinee;
comparing the biological object information read in the reading step, and biological object information stored in a biological object information storing unit of a mobile apparatus in order to obtain a personal authentication result of the examinee;
outputting the personal authentication result;
acquiring examination information which is information on an examination performed on the examinee by an examination apparatus; and
controlling operation of the examination apparatus based on the personal authentication result and the examination information.

* * * * *